(12) United States Patent
Snail et al.

(10) Patent No.: US 6,927,850 B1
(45) Date of Patent: Aug. 9, 2005

(54) INFRARED INTEGRATING SPHERE

(75) Inventors: Keith A. Snail, Silver Spring, MD (US); Kevin F. Carr, Sunapee, NH (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/430,132

(22) Filed: Oct. 9, 1987

(51) Int. Cl.$^7$ .............................................. G01N 21/01
(52) U.S. Cl. ...................................................... 356/244
(58) Field of Search ............................... 356/244–246, 356/236, 213–215; 250/343

(56) References Cited

U.S. PATENT DOCUMENTS

| | | | | |
|---|---|---|---|---|
| 3,562,524 A | * | 2/1971 | Moore et al. ............... | 250/343 |
| 3,902,809 A | * | 9/1975 | Sparks ........................ | 356/311 |
| 4,575,252 A | * | 3/1986 | Akiyama ..................... | 356/446 |
| 4,768,390 A | * | 9/1988 | Baker et al. ................ | 73/865.6 |

OTHER PUBLICATIONS

Snail, K., "Reflectometer design using nonimaging optics", Appl. Optics, Dec. 15, 1987, vol. 26, No. 24, pp. 5326–332.
Gindele, K., Kohl, M., Mast, M. "Spectral reflectance measurements using an integrating sphere in the infrared", Appl. Optics, Jun. 15, 1985, vol. 24, No. 12, pp. 1757–1760.
Hanssen, L., "Integrating–sphere system and method for absolute measurement of transmittance, reflectance . . . ", Appl. Optics, 2001, vol. 40, No 19, pp. 3196–3204.
Chenault, D.B., Snail, K.A., Hanssen, L.M., "Improved integrating–sphere throughput with a lens and nonimaging concentrator", Appl. Optics, 1995, vol. 34, No. 34, pp. 7959–7964.
Snail, K.A., Hanssen, L.M., "Integrating sphere designs with isotropic throughput", Appl. Optics, 1989, vol. 28, No. 10, pp. 1793–1799.

Edwards, D.K., Gier, J.T., Nelson, K.E., Roddick, R.D., "Integrating sphere for imperfectly diffuse samples", Applied Optics, vol. 51, 1960, pp. 1279–1288.
Committee on Colorimetry, "Physical Concepts: Radiant Energy and its Measurement", J. Opt. Society of America, vol. 34, No. 4, Apr. 1944, pp. 183–218.
Snail, K. Carr, K., "Optical Design of an integrating sphere–FTS emissometer", Viewgraphs SPIE Conference on Infrared, Adaptive, Synthetic Optical Sys, 1986, 17 pages.
Snail, K, Carr, K., "Optical Design of an integrating sphere–Fourier transform spectrophotometry FTS emissometer", SPIE Proc. Infr., Adap., Syn. Opt Sys, 1986, V 634, pp. 75–83.

* cited by examiner

*Primary Examiner*—Michael P. Stafira
(74) *Attorney, Agent, or Firm*—John J. Karasek; Edward F. Miles; Sally A. Ferrett

(57) ABSTRACT

Disclosed is an integrating sphere for measuring the diffuse reflectivity of material samples in the infrared. The sphere is disposed in an airtight vacuum chamber under an atmosphere that does not absorb in the infrared. The sphere has two positions at which a sample may be mounted, one on a rod at the sphere's center, another on the sphere's wall, each mounting position corresponding to two different modes of testing samples. The rod acts as a mounting pedestal for a center mounted sample, and is rotatably mounted about its elongate vertical axis so that the sample can rotate with the rod in a horizontal plane. The rod penetrates the sphere and the chamber, and terminates in a knob or handle by which the rod can be rotated to position the sample at a preselected angle. Adjacent to the position for wall mounting, there is a sample heater. This configuration allows one to measure diffuse reflectance of a sample as a function of incidence angle and temperature. In the center-mount configuration, the handle enables one to angularly reposition a center mounted sample without the need to vent and replenish the chamber's atmosphere after each test.

13 Claims, 3 Drawing Sheets

INFRARED INTEGRATING SPHERE

BACKGROUND OF THE INVENTION

The optical characteristics of a material are important material properties, and can be used, for instance, to assign optical signatures to well-known objects or classes of objects, and to identify such objects or classes of objects remotely. For an opaque object, i.e., one having zero transmittance, the object's directional emittance can be characterized if one knows the object's directional hemispherical reflectance as a function of object temperature and angle of incidence. Many systems for determining reflectance are known, prominent among which are integrating spheres, which for decades have been used to measure the reflectance of diffusely reflecting materials in the UV, visible, and near IR. Unfortunately, there are no generally agreed upon reflectance standards beyond 2.5 micrometers in the infrared. Consequently the reflective properties of materials in the infrared are not well known, and there is a need for integrating sphere systems which can measure the infrared diffuse reflectivity of materials with efficiency, convenience, and reliability. Infrared measurements are complicated by air having several constituents (e.g. water and carbon dioxide), that absorb at infrared frequencies, which can distort or otherwise make less precise such measurements of diffuse reflectance if the measurements are made in an air atmosphere with a single beam spectrophotometer. Unfortunately, were one to contain any of the present integrating sphere systems in a chamber containing an artificial, non-absorptive atmosphere, one could examine the angular dependence an object's diffuse reflectance only by venting the atmosphere after each test at each angle of incidence, repositioning the object to change the angle of incidence, and recharging the system's artificial atmosphere. This repeated venting and recharging is most inefficient, inconvenient, and uneconomical.

SUMMARY OF THE INVENTION

Accordingly, an object of this invention is to provide a novel integrating sphere testing system that can measure the diffuse reflectance of samples in the infrared.

Another object of the invention is to operate the system in an atmosphere that has virtually no absorptance in the infrared.

Another object of the invention is to enable one to reposition samples within the system by means external to it, so that one can make a plurality of measurements to test the angular dependence of a sample's diffuse reflectance without needing to vent and replenish the system's atmosphere between any of the plurality of measurements.

Another object of the invention is to enable one to selectively vary sample temperature, so at to allow testing of the temperature dependence of the sample's infrared diffuse reflectance. In accordance with these and other objects made apparent hereinafter, the invention provides an integrating sphere disposed in an airtight chamber under an atmosphere that does not absorb infrared frequencies. The sphere has two positions where a sample may be mounted, one at the sphere's center, another on the sphere's wall, each position corresponding to a different mode by which the sphere can measure diffuse reflectance. In one mode, a rod disposed along a radius vector of the sphere acts as a mounting pedestal for a center-mount sample, disposing the sample at the sphere's geometrical center. The rod is rotatively mounted about its elongate axis so that a center-mounted sample can about with the rod is elongate axis. The rod penetrates the sphere and the airtight chamber, terminating in a handle by which the rod can be rotated as above described, enabling one to select the incidence angle of the beam on the center mounted sample. In this mode one can reposition the pedestal to systematically examine the angular dependence of a specimen's diffuse reflectance. In addition, a reference or standard can be mounted back-to back with the sample to be measured. By having the positioning handle of the rod external to the test chamber, one can angularly reposition the sample in the sphere externally and without the need to vent and replenish the atmosphere in the apparatus for each angular measurement. In the wall-mount mode, a sample is placed on the sphere's wall, and one uses the sphere's wall as the reference. Adjacent to the wall-mount position is a heater for varying sample temperature, with which one can test the temperature dependence of the diffuse reflectance of the wall mounted sample. The ability to mount samples in either of two modes enables one to compare the diffuse reflectance of the center mounted sample against an identical wall mounted sample for purposes of calibrating data taken in one mode by that taken in the other.

BRIEF DESCRIPTION OF THE DRAWINGS

A more complete appreciation of the invention and many of the attendant advantages thereof is readily obtained by reference to the following detailed description, when considered in connection with the accompanying drawings.

DETAILED DESCRIPTION OF THE PREFERRED EMBODIMENT

Figure 1:
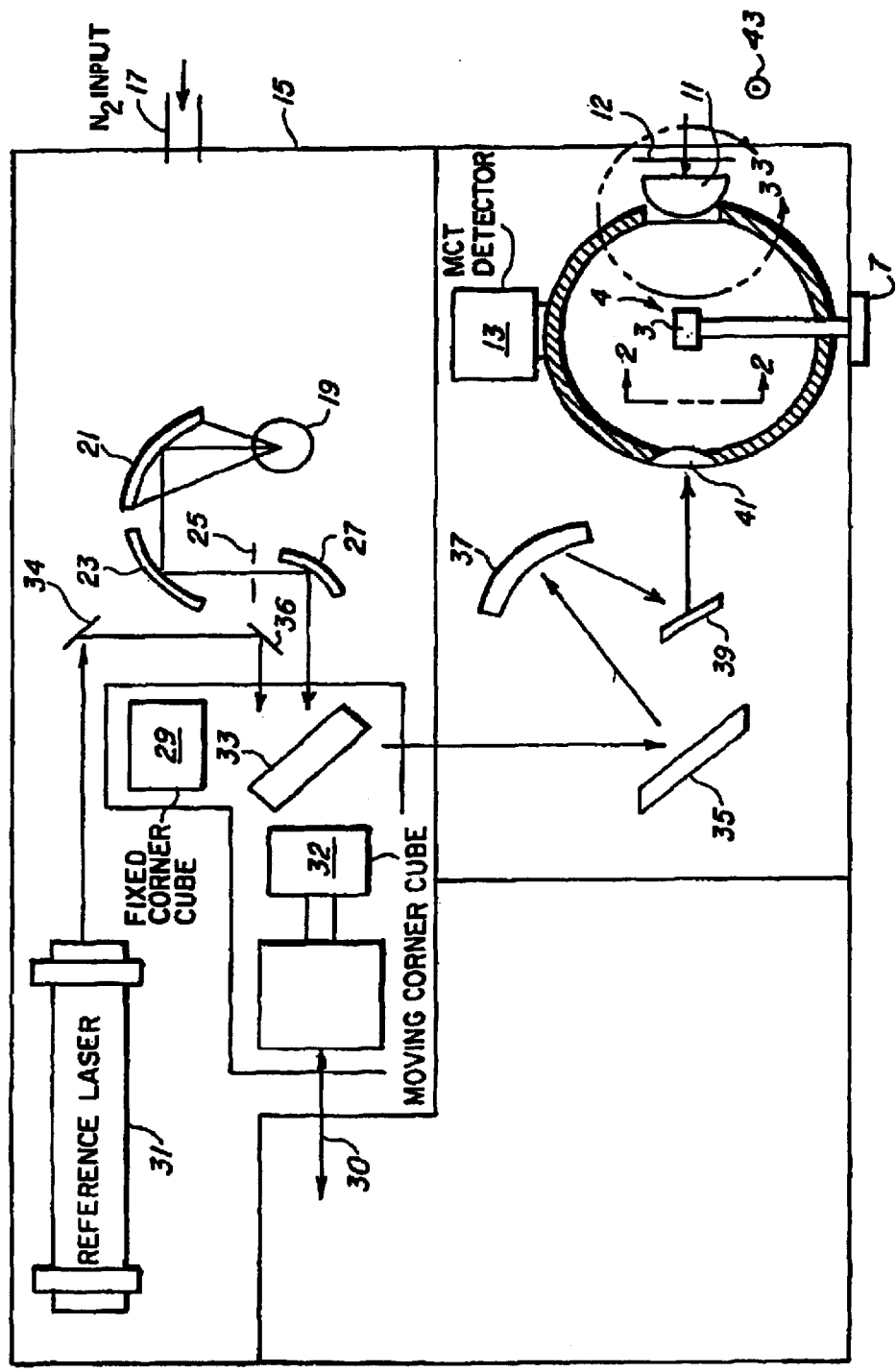
FIG. 1 is a top schematic view, partly in section, of a measuring system employing the instant invention.

Referring now to the drawings, wherein like reference numerals designate identical or corresponding parts throughout the several views, and with particular reference to FIG. 1, an integrating sphere 1 is shown disposed within an airtight chamber 15 under a non-absorptive atmosphere fed in at 17. Nitrogen is preferred because it has virtually no absorptance in the infrared, and as such provides a far better atmosphere for chamber 17 than, e.g., air, which contains much water vapor and carbon dioxide, each of which has characteristic infrared frequencies, and whose absorbtance would degrade infrared measurements taken by sphere 1. Chamber 15 has an appropriate door (not shown), so that one can get to the interior of sphere 1 between tests. Sphere 1 is a metal shell of, for example, nickel, whose inner surface is Lambertian (diffusely reflective). Such a surface can be generated by plating a highly reflective (preferably 95% or greater reflectivity) material onto a pre-roughened surface. In a preferred embodiment, the plating on the inner surface of sphere 1 is gold, an especially good choice not only because of its high reflectivity, but also because its optical properties are generally stable with time. The desired roughness (coarseness) is generated by grit blasting or other conventional techniques. The coarseness of this roughening must be such that the height of micropeaks on sphere 1's inner surface and the distance between such peaks, is of the same order of magnitude as, or larger than, the wavelengths of light to be diffused, and, of course, small with respect to the diameter of any light beam to be input into sphere 1. Surfaces of coarseness appropriate for infrared wavelengths are readily produced with known methods. The gold plate can be applied by any known process, such as chemical ("wet") electroplating. Sphere 1 preferably has a plurality of ports (not shown) which can be closed by conventional removable plugs (not shown) which have inner surfaces geometrically conformable with, and optically identical to, the inner surface of sphere 1. Such ports enable one to practice the "removable cap technique" for measuring the reflectivity of sphere 1's inner surface, this technique well known to those skilled in the art. One skilled in the art may also selectively place the ports so that they may facilitate specular measurements using sphere 1 by acting as specular subtraction ports. As illustrated in FIG. 1, sphere 1 contains a pair of sample mounts 3 and 11, a sample at 3 being disposed at the center of sphere 1 on elongated pedestal 5, and a sample at 11 being disposed on sphere 1's wall. (FIG. 1 additionally shows a sample 4 located at center-mount position 3.) Pedestal 5 penetrates chamber 15 in an airtight manner and has a termination 7 disposed outside chamber 15. Termination 7 is preferably a precision vernier, and enables one to rotate pedestal 5 and a sample 4 mounted at 3 externally of chamber 15 in a place perpendicular to the elongate length of pedestal 5. Pedestal 5 and sample mount 3 should have as small an area as possible, and be coated with the same material that coats the surface of sphere 1. A wall-mounted sample at 11 is mounted on the inner wall of sphere 1, and has adjacent to it a heating element 12 which, in a preferred embodiment, is a simple resistive (joule) heater. Penetrating sphere 1 so as to be exposed to sphere 1's inner surface is a conventional infrared detector 13 which is disposed immediately above and in line with the elongate axis of pedestal 5. Pedestal 5 removably penetrates sphere 1 and chamber 15 so that one can remove pedestal 5 and operate the system in the wall-mount mode. Of course, in the wall-mount mode the opening in sphere 1 through which pedestal 5 would extend is closed by a plug (not shown) whose inner surface is geometrically conformable and optically identical to that of sphere 1. Likewise, in the center mount mode wall mount 11 is removed and similarly plugged.

Also disposed within the atmosphere of chamber 15 is a radiation source 19, preferably silicon carbide, which is heated in any conventional manner, e.g., by a resistive (joule) heater (not shown). Source 19 is disposed at the focus of parabolic mirror 21, and upon source 19 being heated, the electromagnetic radiation generated by source 19 is columnated by mirror 21 and directed to parabolic mirror 23, which in turn directs the radiation to variable iris 25 disposed at the focus of parabolic mirror 23. Light passing through iris 25 is reflected off of parabolic mirror 27, which directs the light to a conventional (e.g., potassium bromide) beam splitter 33, which directs a portion of the light to integrating sphere 1 via mirrors 35, 37, 39.

Beam splitter 33 is disposed at a 45° angle to both fixed corner cube 29, and corner cube 32 that can move linearly along direction 30 at a 45° angle to beam splitter 33. The subsystem formed by corner cubes 29, 32, and beamsplitter 33 is conventional in the art and is used to determine the frequency content of the light input to sphere 1, and the magnitude of signals at these frequencies, so as to measure the total energy input into sphere 1 during any test. As light from mirror 27 impinges upon beam splitter 33, a portion of the light is directed to corner cube 29, and another portion to corner cube 32. A portion of light reflected from corner cubes 29, 32 is recombined and directed on to mirror 35. By measuring in any known manner the respective distances of corner cube 29 and 32 from beamsplitter 33, one knows the phase angle between the two interference signals in the interferometer. With this knowledge, and the interference pattern, one can use conventional Fourier analysis to determine the spectral distribution and intensity of the light incident upon mirror 35, and hence input into sphere 1. Helium-neon laser 31 can also direct light to beam splitter 33 via mirrors 34 and 36. The light from laser 31 is of a precisely known frequency, and hence serves as an excellent standard by which to determine the position of moving corner cube 32. Sphere 1 can be linearly translated along the line of sight of port 41, mount 4, and mount 11 at least a distance equal to the distance between center mount 3 and wall mount 11 so that, whether one uses the center or wall mount mode, the sample of either mode "sees" an optically identical beam through port 41.

Figure 2:
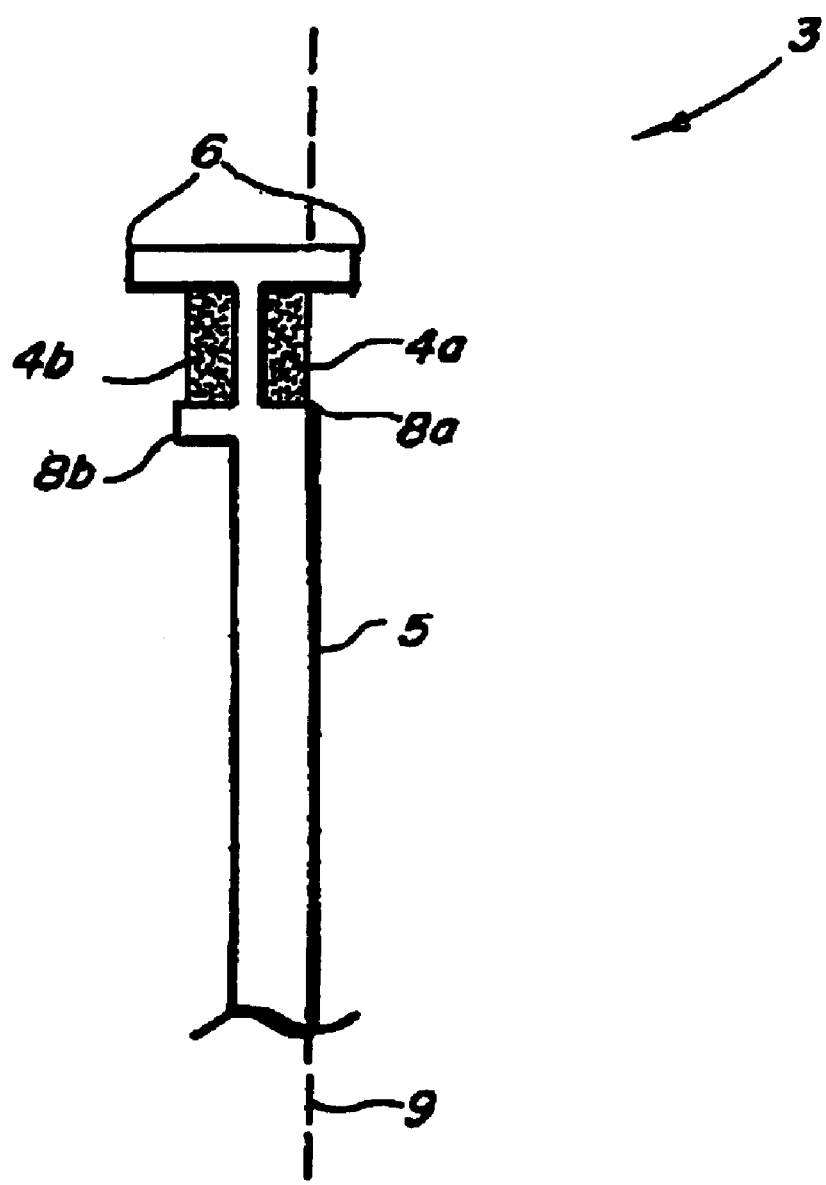
FIG. 2 is a view in the direction of lines 2—2 of FIG. 1.

With particular reference to FIG. 2, more detail of the center mount 4 is shown, which has ledges 8a, 8b upon which are mounted sample 4a and known reference 4b respectively. Ledge 4a is adapted to align the face of sample 4a with sphere 1's centerline 9, so that a point of the face of sample 4a is coincident with sphere 1's center, and rotating of pedestal 5 rotates samples 4a's face about centerline 9, and sphere 1's center. Sample 4b is similarly mounted, but, as seen in FIG. 2, recessed slightly from centerline 9, so that, when pedestal 5 rotates to place sample 4b in the line of sight of opening 41, sample 4b is slightly nearer the incident light beam than would be 4a. Because sample 4b is a reference, one has no need to measure the angular dependence of its reflectance, and experience teaches that this, combined with the small magnitude of offset from axis 9, introduces no significant error into system measurement. Mount 4 also has lip 6 directly above samples 4 and obscuring the line of sight between the samples and detector 13 (FIG. 1). Lip 6 prevents direct reflection from 4a or 4b into detector 13, ensuring that all light incident upon detector 13 is reflected from the surface of sphere 1.

Figure 3:
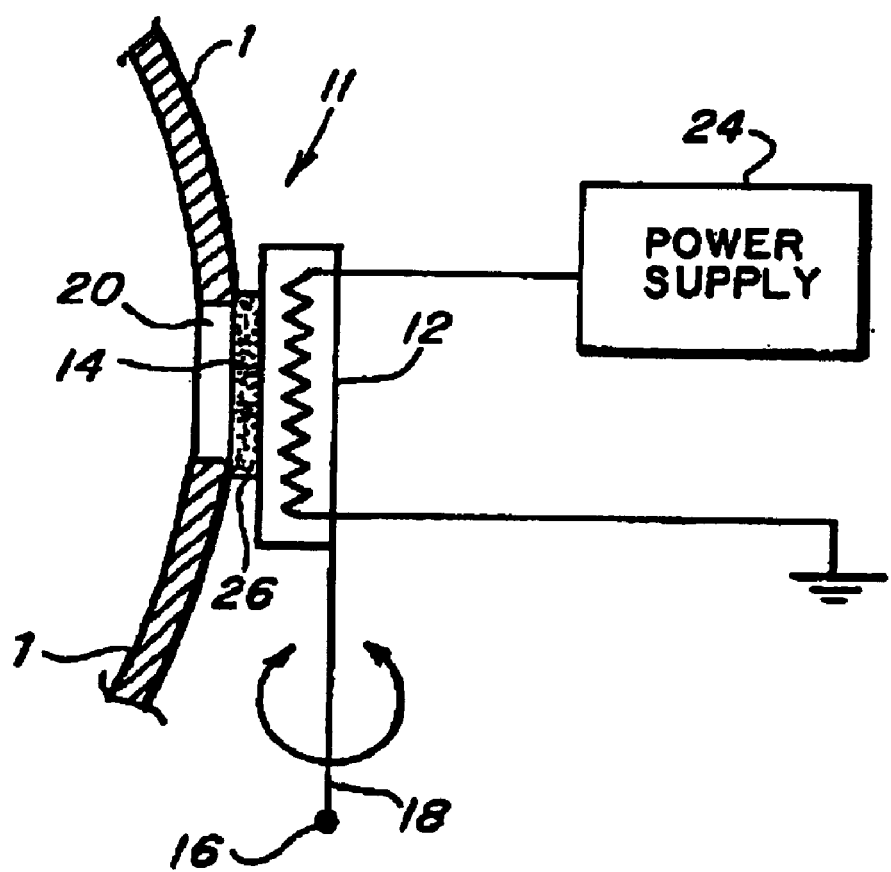
FIG. 3 is a detail of the portion of FIG. 1 encircled by line 3—3.

With particular reference to FIG. 3, the details of a preferred embodiment of wall-mount 11 are shown. Sample 14 is releasably held abutingly adjacent to port 20 of sphere 1, in the line of sight of input port 41 (FIG. 1), by arm 18 of coil spring 18. Preferably sandwiched between sample 1 and arm 18 is heater 12 for controlling the temperature of sample 14. Thermocouple 26 is interlocked (by a conventional means not shown) with power supply 24 for heater 12 so that the power output of supply 24 may be automatically adjusted to control the temperature of sample 14 precisely. This configuration also physically isolates heater 12 from sphere 1 by an insulating dead air space, preventing direct heating of sphere 1 which could result in black-body radiation from sphere 1's inner surface.

In operation, one can measure the reflectance of sample material placed either at sphere 1's center 3, or on its wall at 11. When testing a sample disposed in wall mount 11 sphere 1 is initially positioned with the sample of unknown diffuse reflectance mounted at 11. Light from silicon carbide source 19 is directed to port 41, and tithe sample, which is positioned at 11 as above described, and the flux reflected by the sample at 11, impinges on the inner surface of sphere 1, the magnitude of which is measured by detector 13 after both single and multiple reflections off the inner surface of sphere 1. Sphere 1 is then pivoted in direction 43 about port 41 so as to remove the sample and mount 11 from port 41's line of slight in favor of a portion of sphere 1's gold inner surface, and the measurement repeated. (Direction 43 is perpendicular to the plane formed by the elongate length of pedestal 5 and the line of sight between port 41 and sample 4—the plane of the drawing sheet on which FIG. 1 is set forth.) Pivoting sphere 1 in this manner maintains the symmetry between detector 13 and the sample of the first measurement, and detector 13 and the portion of sphere 1's surface of the second measurement, thus reducing systematic error. In this manner the relative diffuse reflectance of the wall mounted sample and sphere 21's gold surface is measured, and the reflectance of the gold surface is determined using the "removable cap technique" which can now serve as the reference for later measurements. Thus calibrated, one can repeat this procedure to measure any sample at 11 of unknown diffuse reflectance using the inner surface of sphere 1 itself as the reference. Heater 12 can vary the temperature of a sample at 11 to allow one to investigate the temperature dependence of such a sample's diffuse reflectance.

For a sample center-mounted at 3, one inserts pedestal 5 carrying sample 4 as above described. Manipulation of termination 7 of pedestal 5 sets the angle of incidence at which light passing through opening 41 hits sample 4. In this manner, a series of measurements of sample 4 may commence by turning standard portion 4b toward opening 41 (hence opaquing portion 4a) and using the standard to calibrate the system. Thereafter, sample portion 4a may be turned towards opening 41, and a series of measurements taken at various angles of incidence so as to test the angular dependence of the sample portion 4a's diffuse reflectance. Because incidence angle is set by external termination 7, one need not purge and replenish the nitrogen atmosphere in chamber 15 between each re-setting of angular position, a great economy as well as a great convenience to the operator.

Obviously numerous additional modifications and variations of the present invention are possible in light of the above teachings. It is therefore to be understood that, within the scope of the appended claims, the invention may be practiced other than described specifically herein above.

What is claimed and desired to be secured by Letters Patent of the United States is:

1. A system comprising:
   an integrating sphere;
   an airtight chamber effective to provide the inside of said chamber with a non-air atmosphere of preselected composition; and
   a pedestal effective to mount said sample at the center of said sphere, said pedestal comprising angular adjustment means for rotating said sample in said sphere, said angular adjustment means comprising a termination for enabling said angular adjustment means to rotate said sample in said sphere from outside said chamber.

2. The system of claim 1, wherein said pedestal comprises a mount effective to mount said sample and a reference sample back-to-back on said pedestal.

3. A system comprising:
   an integrating sphere;
   an airtight chamber effective to provide the inside of said chamber with a non-air atmosphere of preselected composition;
   a clamp for mounting said sample on the inside wall of said integrating sphere,
   wherein said integrating sphere has a port passing through the wall of said sphere for exposing said sample to light flux incident upon said port from the inside of said sphere, and wherein said clamp forces said sample into fixed abutment with said port; and
   heating means for heating said sample, said clamp being effective to mount said heating means in thermal contact with said sample effective to heat said sample to a preselected temperature, said clamp being effective to mount said heating means physically distant from said wall.

4. The system of claim 3 wherein said clamp is a tension spring having an arm effective to abuttingly clamp said heating means against said sample and said sample against said wall, at least a portion of said heating means being disposed between said sample and said arm.

5. The system of claim 3 wherein said heating means is an electrical resistive heater.

6. In an integrating sphere, said sphere having a wall and a port for passing light flux from the inside of said sphere to the outside, means for mounting a sample effective to expose at least a portion of said sample to light flux exiting from said interior, said means for mounting comprising a clamping means for forcing said sample into fixed abutment with said port, wherein said means for mounting is a pedestal effective to mount said sample at the center of said sphere, said pedestal comprising an angular adjustment means for rotating said sample in said sphere, said angular adjustment means comprising a termination for enabling said angular adjustment means to rotate said sample in said sphere from outside a chamber.

7. The system of claim 6 wherein said pedestal comprises a mount effective to mount two sample portions back-to-back on said pedestal.

8. The system of claim 7 further comprising:
   a clamp for mounting a sample on the inside wall of said integrating sphere.

9. The system of claim 8 wherein said integrating sphere has a port passing through the wall of said sphere, said means for mounting is effective to expose said sample to light flux incident upon said port from the inside of said sphere, and wherein said clamp maintains said sample into fixed abutment with said port.

10. The system of claim 9 wherein said means for mounting comprises a heater for heating said sample, said clamp is effective to mount said heating means in thermal contact with said sample effective to heat said sample to a preselected temperature, said clamp being effective mount said heating means physically distant from said wall.

11. The system in claim 10 wherein said clamp is a tension spring having an arm effective to abuttingly clamp said heater against said sample and said sample against said wall, at least a portion of said heater being sandwiched between said sample and said arm.

12. The system in claim 11 wherein said heater is an electrical resistive heater.

13. The system as in claim 1, further comprising:
   a clamp for mounting a sample on an inside wall of the integrating sphere.

* * * * *